United States Patent
Uhari et al.

[11] Patent Number: 6,066,677
[45] Date of Patent: *May 23, 2000

[54] USE OF XYLITOL AND PHARMACEUTICAL COMPOSITIONS THEREFOR

[75] Inventors: Matti Uhari; Tero Kontiokari, both of Oulu, Finland

[73] Assignee: Leiras Oy, Turku, Finland

[ * ] Notice: This patent is subject to a terminal disclaimer.

[21] Appl. No.: 09/180,761

[22] PCT Filed: Jul. 16, 1997

[86] PCT No.: PCT/FI97/00448

§ 371 Date: Jan. 15, 1999

§ 102(e) Date: Jan. 15, 1999

[87] PCT Pub. No.: WO98/03165

PCT Pub. Date: Jan. 29, 1998

Related U.S. Application Data

[63] Continuation of application No. 08/685,506, Jul. 24, 1996, Pat. No. 5,719,196.

[51] Int. Cl.[7] .................................................. A61K 31/045
[52] U.S. Cl. ............................................................. 514/738
[58] Field of Search .............................................. 514/738

[56] References Cited

U.S. PATENT DOCUMENTS 4,767,785  8/1988  Georgieff ................................. 514/561
5,719,196  2/1998  Uhari et al. ............................. 514/738

FOREIGN PATENT DOCUMENTS

| 0 339 508 A1 | 11/1989 | European Pat. Off. . |
| 2 606 533 | 8/1976 | Germany . |
| WO 96/08232 | 3/1996 | WIPO . |
| WO 97/17089 | 5/1997 | WIPO . |

OTHER PUBLICATIONS

Health Fact, vol 21,(211), 1–2, Dec. 1996.
Winter, G, Brit.Med.J., vol. 313 (7066), 1183–4, Nov. 9, 1996.
Kontiokari et al., "Effect of Xylitol on Growth of Nasopharyngeal Bacteria in Vitro," 39 *Antimicrobial Agents and Chemotherapy* 1820–1823 (Aug. 1995).

*Primary Examiner*—Rebecca Cook
*Attorney, Agent, or Firm*—James C. Lydon

[57] ABSTRACT

A method of treating respiratory infections or complications derived therefrom in mammals, especially acute otitis media in humans, which includes administering to the mammal an effective amount of xylitol. The invention further concerns the use of xylitol for the preparation of a pharmaceutical composition for the treatment of respiratory infections or complications derived therefrom in mammals. One or more therapeutically active agents may optionally be added to the pharmaceutical composition, which can be a solid preparation, such as chewing gum, a powder or tablet, or a liquid preparation.

10 Claims, 3 Drawing Sheets

6,066,677

USE OF XYLITOL AND PHARMACEUTICAL COMPOSITIONS THEREFOR

This is a 371 of PCT/FI97/00448 filed Jul. 16, 1997 which is a continuation of 08/685,505 filed Jul. 24, 1996, now U.S. Pat. No. 5,719,196.

FIELD OF THE INVENTION

The present invention relates to a means of treating respiratory infections or complications derived therefrom, in mammals, and more particularly, to a method of preventing acute otitis media in humans involving oral administration of xylitol. The invention further relates to the use of xylitol for the preparation of a pharmaceutical compositions for the treatment of respiratory infections or complications derived therefrom in mammals. The invention also concerns pharmaceutical compositions comprising xylitol.

BACKGROUND OF THE INVENTION

The publications and other materials used herein to illuminate the background of the invention, and in particular, cases to provide additional details respecting the practice, are incorporated by reference.

Xylitol has been classified as a polyol or a sugar alcohol and is referred to as birch sugar, because it can be produced from birch. Xylitol occurs widely in nature, although the concentrations are low. Natural sources of xylitol include plums, strawberries, rasberries and rowan berries (1). Xylitol has the same relative sweetness as sucrose, and it has been used as a sugar substitute for dietary and medical purposes. Because of its five-carbon sugar alcohol structure, xylitol is unsuitable as a source of energy for most oral micro-organisms, such as *Streptococcus mutans* (2). Yet, most *S. mutans* strains are, via the fructose phosphotransferase system, able to transport xylitol into the cell, where it is phosphorylated into xylitol-5-phosphate, which then has to be expelled from the cell (3). This metabolically futile xylitol cycle consumes energy stores of the call and is thought to be responsible for the inhibition of the growth of *S. mutans* observed both in vitro and in vivo when exposed to xylito (4).

Regular consumption of xylitol has been shown to reduce the incidence of dental caries, although the mechanisms are not completely understood (5–8). The most significant effect so far demonstrated is the ability of xylitol to reduce the growth and acid production of *S. mutans*, which is the most important bacterium taking part in the pathomechanism of dental caries (9).

We have previously found that xylitol inhibits the growth of *S. pneumoniae* and *S. mutans* in vitro during their logarithmic growth phase. This effect is dosedependent. We similary observed a slight postexponential inhibition of growth with beta-hemolytic streptococci, but not with *Haemophilus influenzae*, nor with *Moraxella catarrhalis* (10). The disclosure of this reference 10 is hereby incorporated as reference.

*S. pneumoniae* is an important etiologic agent of bacterial pneumonia, sepsis and meningitis (11). It accounts for about 30% of all acute otitis media (AOM) episodes, as estimated by bacterial cultures from the middle-ear (12–13). This figure may be even higher when more sensitive methods of detecting bacteria are applied (14). At the age of 3 years, 20 to 40% of healthy children carry pneumococci in their nasopharynx. This carriage increases during acute infections (15). Nasopharyngeal carriage of pneumococci has been shown to be a predisposing factor for AOM in children in the day care setting (15).

SUMMARY OF THE INVENTION

The present invention relates to the use of xylitol for the treatment of respiratory infections or complications therefrom in mammals, especially acute otitis media in humans.

The invention further relates to the use of xylitol for the preparation of a pharmaceutical composition for the treatment of respiratory infections or complications derived therefrom in mammals.

Furthermore, this invention concerns a pharmaceutical composition comprising a therapeutically effective amount of xylitol in combination with a pharmaceutically acceptable excipient, wherein said composition is either a) a liquid preparation, which optionally comprises a viscosity increasing agent, or b) a dry preparation in the form of powder, tablet or the like.

The present invention is based on the surprising discovery that xylitol exhibits a growth inhibiting effect against pneumococci which reduces the incidence of acute otitis media.

DETAILED DESCRIPTION OF THE INVENTION

Figure 1:
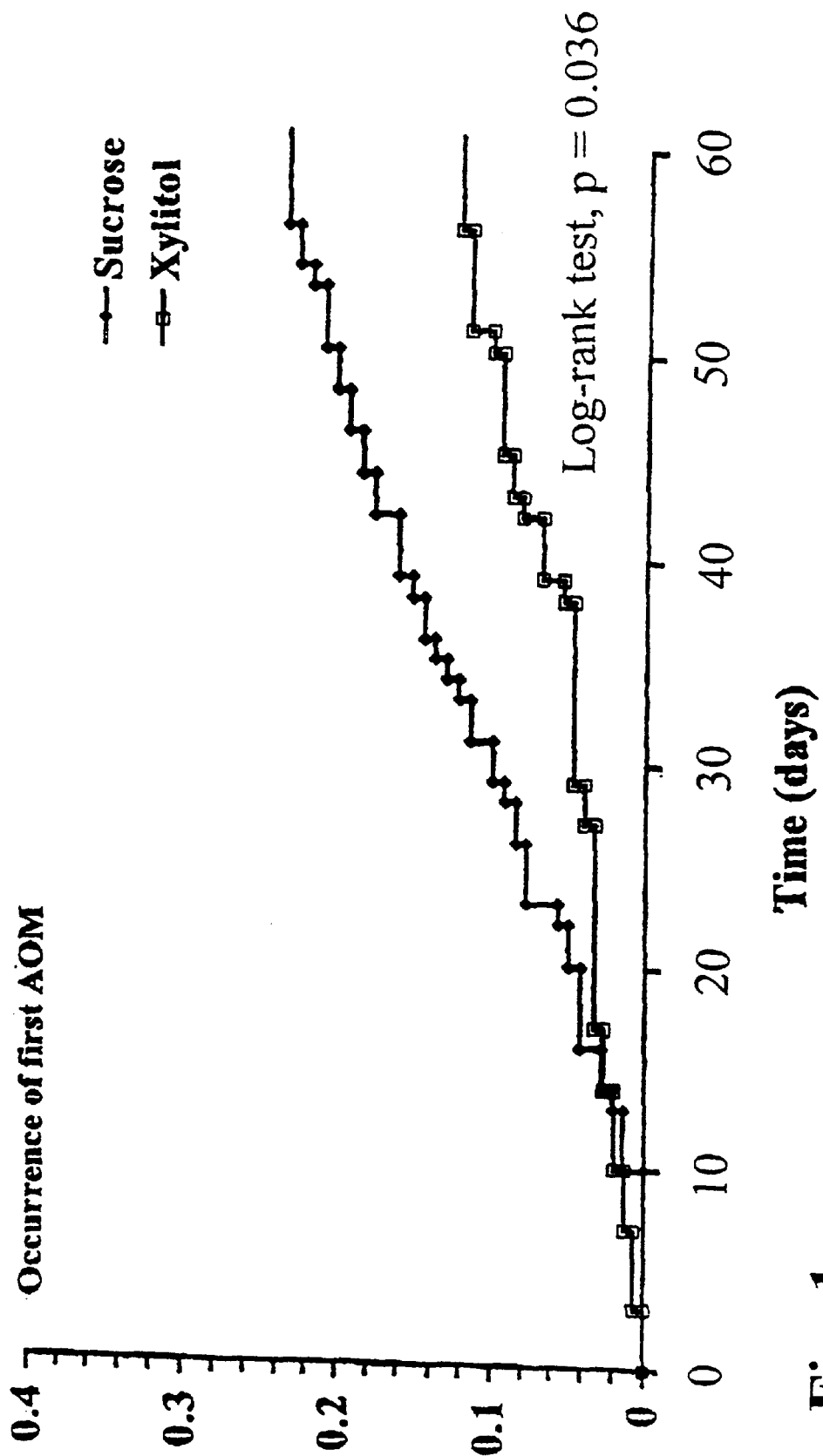
FIG. 1 shows graphically the cumulative occurrence of first acute otitis media (AOM) attack during a two-month monitoring period in a xylitol group and a reference sucrose group.

In accordance with the present invention there is provided a method of treating at least one respiratory infection or complication therefrom in manuals which comprises orally administering to the mammal an effective amount of xylitol.

As used herein respiratory infections include acute otitus media (AOM), upper respiratory infection, acute bronchitis, sinusitis and conjunctivitis.

As used herein treating means first of all preventing but is not limited thereto.

According to a preferred embodiment of the invention there is provided a method of preventing acute otitis media in humans which comprises orally administering to the human an effective amount of xylitol.

The xylitol may be formulated as a solid or liquid preparation.

The solid preparation may be in the form of, for example, tablets, powders or lozenges or chewing gums, and may contain conventional excipients and fillers.

The liquid preparation may be in the form of, for example, an aqueous solution or syrup, and may contain conventional additives.

The suitable daily dose of the xylitol may vary widely depending on, for example, the administration form, the age and condition of the human being subjected to the treatment. A suitable daily dose for children by using xylitol in oral preparations may range from about 6 grams to about 10 grams, especially from about 8 grams to about 9 grams.

EXPERIMENTAL

Experiment 1
Effect of xylitol chewing gum

Our hypothesis that the growth inhibiting effect of xylitol against pneumococci could reduce the pneumococcal carriage rates and also reduce the incidence of AOM, was evaluated in a double-blind randomized trial using chewing gum as the vehicle to deliver xylitol to children. The study was a randomized double-blind trial performed in 11 day care centers in the city of Oulu. The study protocol was evaluated and approved by the Ethical Committee of the Health Center of Oulu. The parents of the participating children gave informed consent. The study material was donated by Leaf-Huhtamäki (Leaf-Huhtamäki Co., Turku, Finland) and was sent to us packaged in number coded cartridges containing 60 numbered boxes with 10 pieces of chewing gum, each sweetened with either xylitol or sucrose according to a random sequence produced using a random number table. To ensure equal numbers of children in the sucrose and xylitol groups in each of the day care centers, we used block randomization with a block size of four (1). The children were numbered in the order they entered the study and each child received one cartridge according to his/her number and was instructed to chew two pieces 5 times (one box) per day after meals, making a total dose of 8.4 g xylitol per day. The chewing lasted until there was no taste left or at least 5 minutes. The parents were asked to proceed with the normal feeding routines, but to avoid the use of xylitol during the study. If dental caries was noticed while taking the nasopharyngeal samples, the child was advised not to participate in the study because of the sucrose content of the placebo chewing gum.

Results

A total of 336 children were enrolled in March 1995. There were 30 drop-outs, which left 306 children, 149 in the sucrose group and 157 in the xylitol group, eligible for analysis. The results obtained are summarized in Table 1.

TABLE I

Respiratory infections recorded by the treating physician

| Diagnose | Sucrose (n = 149) Number | Xylitol (n = 157) | P-value* |
|---|---|---|---|
| Acute otatis media** | 43 | 22 | 0.033 |
| Upper respiratory infection | 14 | 11 | 0.33 |
| Acute bronchitis | 5 | 2 | 0.37 |
| Sinusitis | 2 | 3 | 0.70 |
| Conjuctivitis | 3 | 1 | 0.29 |

*Man-Whitney U-test
**Number of the children with at least one event of AOM was 31 in sucrose vs. 19 in xylitol group, 8.7% difference with 95% CI 0.4–17.0% (p < 0.04).

The numbers of upper respiratory tract infections, acute bronchitis, sinusitis and conjunctivitis leading to visits to 41 different physicians were somewhat smaller in the xylitol group than in the sucrose group. The total number of AOM attacks was 43/149 among the children in the sucrose group as comnpared to 22/157 among the children who received xylitol. The number of children with at least one episode of AOM was 31/149 (20.8%) in the sucrose group and 19/157 (12.1%) among those who received xylitol (difference 8.7%, 95% CI 0.4–17.0%, p=0.040). The occurrence of the first AOM attack differed significantly between the groups when tested with the log-rank test (p≠0.036) (FIG. 1) and was associated with the amount of xylitol used: those who experienced AOM had forgotten their xylitol chewing gums significantly more often than those who had not had any AOM events, the means of forgotten xylitol being 48.8 g vs. 22.4 g (difference 26.4 g, 95% CI 5.7–47.1 g, p=0.024), respectively. Within the sucrose group, there was no significant association between the occurrence of AOM and the use of sucrose chewing gums, and the mean amount of gum forgotten by those with AOM was 25.9 g as compared to 28.0 g of those who had not had any AOM attacks (difference −2.2 g, 95% CI−27.0–22.7 g, p=0.68).

The total number of antimicrobial medications prescribed in the xylitol group was 34 as compared to 60 in the control group. At least one period of antimnicrobials was received by 43/149 (28.9%) children in the sucrose group and 29/157 (18.5%) children in the xylitol group (difference 10.4% with 95% CI for the difference 0.9%–19.9%, p=0.032).

All the possible the risk factors of AOM, i.e. parental education and smoking, breast feeding, use of pacifier, otitis-prone sibling, previous history of AOM, previous use of xylitol, and nasopharyngeal carriage of pneumococci were controlled using a logistic multivariate analysis. When at least one attack of AOM was the dependent variable of the model, the type of sugar given to the child significantly associated with the occurrence of AOM in such a way that the children receiving xylitol had fewer attacks of AOM (p=0.045).

Two children in our trial stopped the use of xylitol because of complaints of diarrhea. Yet, the recorded number of diarrhea episodes and the mean duration of diarrhea were similar in the xylitol and sucrose groups. The dose of 8.4 g xylitol used in our trial is markedly less than the maximal dose previously reported to be tolerable (17).

Respiratory infections, and especially AOM, in children are the main reason for the use of oral antimicrobials (18). The emergence of multi-drug resistant strains of *S. pneumoniae* substantiates the need for new approaches in preventing bacterial infections. The results above show that xylitol, a well-tolerated food additive, is effective in preventing AOM in children.

Experiment 2
A three-month follow-up study

To confirm our earlier observation that xylitol chewing gum prevents acute otitis media (19) and to evaluate the efficacy of other xylitol preparations we made a controlled three-month follow-up study.

Altogether 858 children were randomly allocated to receive sucrose chewing gum (n=178), xylitol chewing gum (n=179), xylitol lozenge (n=176), control syrup (n=165) or xylitol syrup (n=160). All the preparations were given five times per day. The daily dose of xylitol in the study groups varied from 8.4 g (chewing gum) to 10 g (syrup). The children in the control groups got 0.5 g xylitol per day. The trial was blinded between the chewing gum groups and syrup groups. An open comparison was made between lozenge group and control chewing gum group. The daily symptoms were followed by using symptom sheets, and the children were examined with tympanometry and pneumatic otoscopy each time they got any symptoms of infections.

Results

During the three-month monitoring period, at least one event of acute otitis media was experienced by 68/165 (41.2%) of the children who received control syrup as compared to 45/160 (28.1%) of the children receiving xylitol syrup (31.8% decrease, p=0.013).

Figure 2:
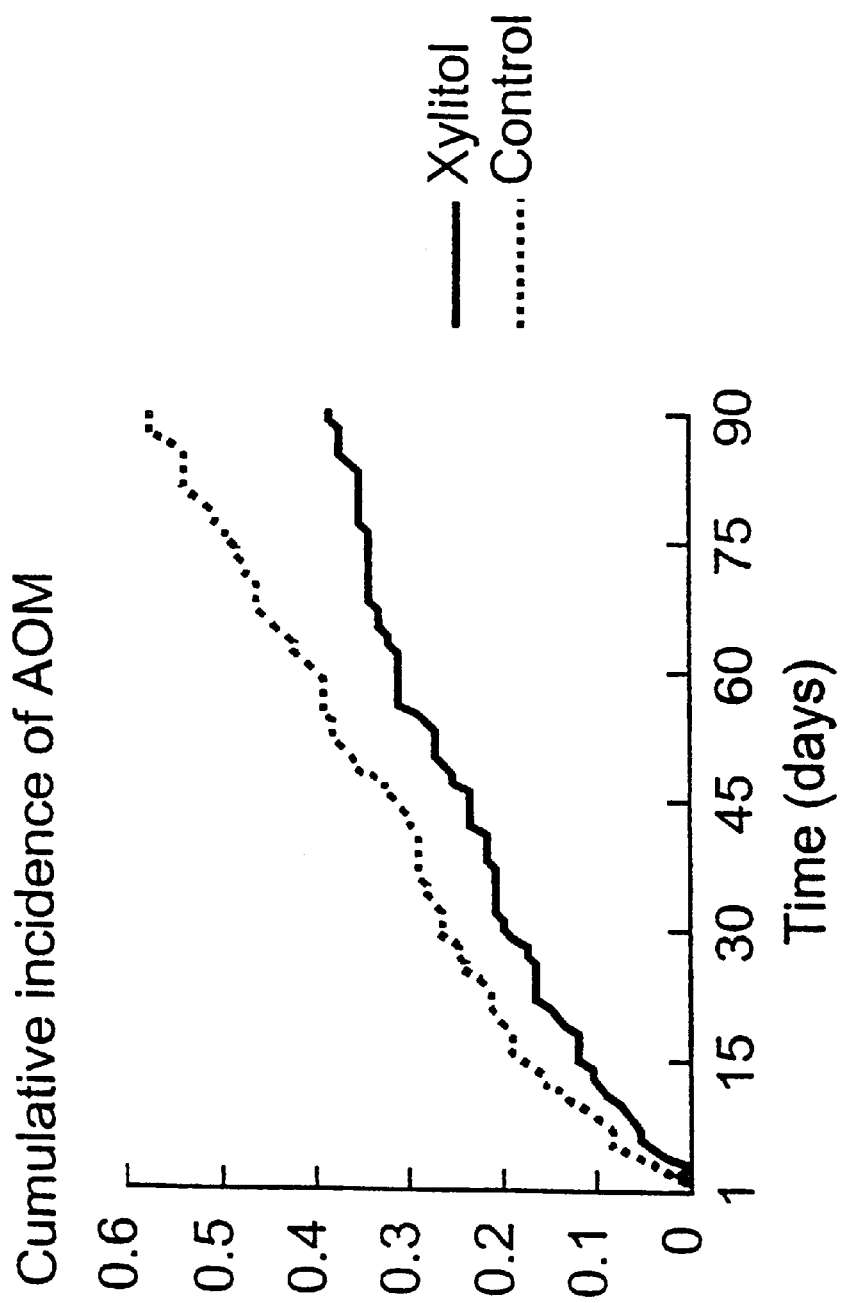
FIG. 2 shows the cumlative indicience of acute otitis media (AOM) versus time during the 3-month follow-up among children who received control syrup (Control) or xylitol syrup (Xylitol).

FIG. 2 demonstrates the probability of acquiring acute otitis media (AOM) during the 3-month follow-up among children who received control syrup (Control) or xylitol syrup (Xylitol). The occurrence is statistically significantly lower among those who received xylitol syrup (P=0.0396, log rank test).

Otitis media occurred in 47/178 (26.4%) of the children who received sucrose chewing gum as compared to 26/179 (14.5%) of those receiving xylitol-containing chewing gum (45.1% decrease, p=0.005). In the Lozenge group 36/176 (20.5%) experienced acute otitis media (22.3% decrease as compared to the sucrose chewing gum group, p=0.186).

Figure 3:
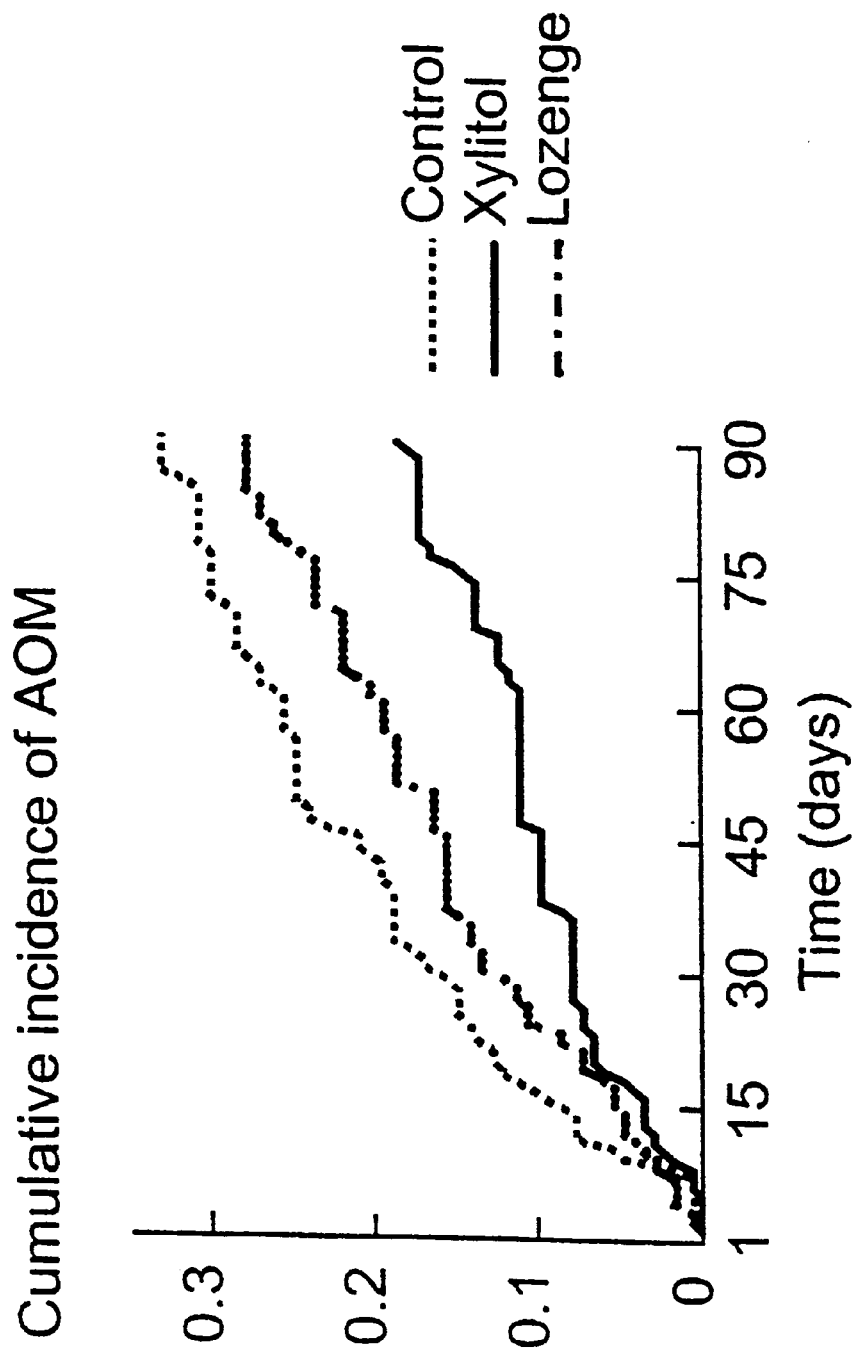
FIG. 3 shows the cumulative indicience of acute otitis media (AOM) during the 3-month follow-up among children who received control chewing gum (Control), xylitol gum (Xylitol) or xylitol lozenges (Lozenge).

FIG. 3 demonstrates the probability of acquiring acute otitis media (AOM) during the 3-month follow-up among children who received control chewing gum (Control), xylitol gum (Xylitol) or xylitol lozenges (Lozenge). The occurrence is statistically significantly lower among those who received xylitol chewing gum as compared to Control (P=0.009, log-rank test) but not between Lozenge and Control groups (P=0.3624, log-rank test).

Xylitol was well tolerated even though there were more abdominal discomfort among children who received xylitol as compared to control preparations. The results show that xylitol when given in syrup or in chewing gums was effective in preventing acute otitis media.

The following non-limiting examples further demonstrate pharmaceutical compositions according to the invention.

EXAMPLE 1

Liquid Formulations Containing Xylitol a) Xylitol Containing Mixture without Addition of Viscosity Increasing Substance (composition per milliliter of mixture):

| | |
|---|---|
| Xylitol | 400.00 mg |
| Purified water to give 1 ml | |
| Optional additives: | |
| Ascorbic acid | 1.00 to 3.33 mg |
| Preservatives: | |
| Propyl parahydroxybenzoate | 0.15 mg |
| Methyl parahydroxybenzoate | 1.30 mg |
| Flavoring agents (if necessary): | |
| Orange oil | 0.10 mg |
| (or cranberry juice or the like) | |
| Coloring agents (if necessary): | |
| Quinoline yellow | 0.10 mg | b) Xylitol Containing Mixture Containing a Viscosity Increasing Substance (composition per milliliter of mixture):

| | |
|---|---|
| Xylitol | 50.0 % (m/V) |
| Purified water to give 1 ml | |
| Viscosity increasing polymers (%, m/m): | |
| Sodium carboxymethyl cellulose (NaCMC) | 1 to 6% |
| (the amount depends on the molecule size) | |
| Carbopol-934P | 0.25 to 2% |
| Polyvinyl alcohol (PVA) | 5 to 10% |
| Starch (e.g. potato starch) | 3 to 10% |
| Hydroxyethylcellulose | 0.5 to 3% |
| (the amount depends on the molecule size) | |

Buffer:
Sodium Phosphate Buffer, e.g. 60 mM
Preservatives:

| | |
|---|---|
| Propyl parahydroxybenzoate | 0.15 mg |
| Methyl parahydroxybenzoate | 1.30 mg |
| Flavoring agents (if necessary): | |
| Orange oil | 0.10 mg |
| (or cranberry juice or the like) | |
| Coloring agents (if necessary): | |
| Quinoline yellow | 0.10 mg |

EXAMPLE 2

Xylitol Containing Dosage Powder (Finrexin$^R$) for Treating Cold-related Symptoms

| | |
|---|---|
| General therapeutically active agents: | |
| Acetylsalicylic acid | 500.00 mg |
| Coffein | 60.00 mg |
| Ascorbic acid | 300.00 mg |
| Optional binding agents: | |
| Polyvidone | 1.00 to 250.00 mg |
| or | |
| Hypromellose | 1.00 to 250.00 mg |
| Flavoring agents: | |
| Tartaric acid | about 120.00 mg |
| Sodium chloride | 8.00 mg |
| Sodium citrate | 40.00 mg |
| Blackcurrant | 40.00 mg |
| (other possible flavoring agents are e.g. lemon, eucalyptys, peppermint and menthol) | |
| Sweetening agent: | |
| Sodium cyclamate | 60.00 mg |
| (an alternative sweetening agent is e.g. aspartame) | |
| Coloring agents: | |
| Anthocyanin powder | 30.00 mg |
| or | |
| Quinoline yellow E104 | 2.50 mg |
| Additional ingredients: | |
| Mannitol | 1841.00 to 3500.00 mg |
| Xylitol | 1000.00 to 4500.00 mg |

The weight of one bag of dosage powder is 1000 to 6000 mg.

It will be appreciated that the present invention can be incorporated in the form of a variety of embodiments, only a few of which are disclosed herein. It will be apparent for the person skilled in the art that other embodiments exist and do not depart from the spirit of the invention. Thus, the described embodiments are illustrative and should not be construed as restrictive.

LIST OF REFERENCES

1. Mäkinen K K., Söderling E. A quantitative study of mannitol, sorbitol, xylitol, and xylose in wild berries and commercial fruits. J. Food Sci. 1980;45:367–71.
2. Knuutttila MLE., Mäkinen K K. Effect of xylitol on the growth and metabolism of *Streptococcus mutans*. Caries Res. 1975;9:177–89.

3. Assev S., Rölla G. Evidence for presence of the xylitol phosphotransferase system in *Streptococcus mutans* OMZ 176 by xylitol. Acta Pathol Microbiol Immunol Scand B 1984;92:89–92.
4. Söderling E., Pihlanto-Leppälä A. Uptake and expulsion of 14C-xylitol by xylitol-cultured *Streptococcus mutans* ATCC 25175 in vitro. Scand. J. Dent. Res. 1989;97:511–9.
5. Scheinin A., Mäkinen K K. Turku sugar studies I–XXI. Acta Odontol Scand. 1975;33: Suppl 70:1–351.
6. Scheinin A., Bánóczy J. Xylitol and caries: The collaborative WHO oral disease preventive program in Hungary. Int. Dent. J. 1985;35:50–7.
7. Isokangas P., Alanen P., Tiekso J., Mäkinen K K. Xylitol chewing gum in caries prevention. A field study in children. J. Am. Dent. Assoc. 1988;117:315–20.
8. Kandelman D., Bär A., Hefti A. Collaborative WHO xylitol field study in French Polynesia. Caries Resa. 1988;22:55–62.
9. Vadeboncoeur C., Trahan L., Mouton C., Mayrand D. Effect of xylitol on the growth and glycolysis of acidogenic oral bacteria. J. Dent. Res. 1983;62:882–4.
10. Kontiokari T., Uhari M., Koskela M. Effect of xylitol on growth of nasopharyngeal bacteria in vitro. Antimicrob Agents Chemother 1995;39:1820–3.
11. bruyn GAW., Zegers B J M., van Furth R. Mechanisms of host detense, against infection with *streptococcus pneumoniae*. Clin. Infect Dis. 1992;14:251–62.
12. Luotonen J., Herva E., Karma P., Timonen M., Leinonen M., Mäkelä P H. The bacteriology of acute otitis media in children with special reference to streptoccus pneumoniae as studied by bacteriological and antigen detection methods. Scand. J. Infect Dis. 1981;13:177–83.
13. Harrison C J., Chartstrand S A., Pichichero M E. Microbiologic and clinical aspects of a trial of once daily cefixime compared with twice daily cefaclor for treatment of acute otitis media in infants and children. Pediatr. Infect Dis. J. 1993;12;62–9.
14. Del Beccaro M A., Mendelman P M., Inglis A F. et al. Bacteriology of acute otitis media: A new perspective. J. Pediatr. 1992; 120:81–4.
15. Faden H., Waz M J., Bernstein J m., Brodsky L., Stanievich J., Ogra P L. Nasopharyngeal flora in the first three years of life in normal and otitis-prone children. Ann. Otol. Rhinol. Laryngol 1991; 100:612–5.
16. Pocock, S J. Clinical trials. A practical approach, Chichester: John Wiley & sons; 1983.
17. Akerblom H K., Koivukangas K T., Puukka R., Mononen M. The tolerance of increasing amounts of dietary xylitol in children. Int. J. Vitam. Nutr. Res. 1982;22:53–66.
18. Berman S. Otitis media in children. N. Engl. J. Med. 1995; 332:1560–5.
19. Uhari M, Kontiokari T, Koskela M, Niemelä M. Xylitol chewing gum in preventing acute otitis media. Brit med J 1996; 313:1180–4.

We claim:

1. A method for preventing a bacterial infection in a human, which method comprises orally administering to the human an effective amount of xylitol, wherein said bacterial infection is selected from the group consisting of acute otitis media, upper respiratory infection, acute bronchitis, sinusitis and conjunctivitis.

2. The method of claim 1, wherein the infection is acute otitis media.

3. The method of claim 1, wherein the infection is conjunctivitis.

4. The method of claim 1, wherein xylitol is orally administered in the form of a solid preparation.

5. The method of claim 4, wherein the orally administered form is chewing gum.

6. The method of claim 1, wherein xylitol is orally administered in the form of a liquid preparation.

7. The method of claim 1, wherein xylitol is administered in a daily dosage range of between 6 grams and 10 grams.

8. A method of preventing acute otitis media in a human, which comprises orally administering to the human an effective amount of xylitol in the form of a chewing gum.

9. The method of claim 8, wherein xylitol is administered in a daily dosage range of between 6 grams and 10 grams.

10. The method of claim 9, wherein xylitol is administered in a daily dosage range of between 8 grams and 9 grams.

* * * * *